United States Patent [19]
Reesemann

[11] Patent Number: 5,855,567
[45] Date of Patent: Jan. 5, 1999

[54] CATHETER MANAGEMENT SYSTEM

[75] Inventor: Thomas V. Reesemann, St. Cloud, Minn.

[73] Assignee: SciMed Life Systems, Inc., Maple Grove, Minn.

[21] Appl. No.: 701,743

[22] Filed: Aug. 22, 1996

[51] Int. Cl.⁶ .................................................. A61M 5/00
[52] U.S. Cl. .............................................. 604/171; 604/96
[58] Field of Search ................................. 604/96, 97, 98, 604/102, 103, 171; 606/192, 194

[56] References Cited

U.S. PATENT DOCUMENTS

| | | | |
|---|---|---|---|
| 3,561,445 | 2/1971 | Katerndahl et al. | 128/214.4 |
| 4,397,091 | 8/1983 | Gustavsson et al. | 33/127 |
| 4,401,433 | 8/1983 | Luther | 604/159 |
| 4,820,271 | 4/1989 | Deutsch | 604/99 |
| 5,045,061 | 9/1991 | Seifert et al. | 604/96 |
| 5,100,381 | 3/1992 | Burns | 604/96 |
| 5,117,831 | 6/1992 | Jang et al. | 604/96 |
| 5,154,725 | 10/1992 | Leopold | 604/96 X |
| 5,158,548 | 10/1992 | Lau et al. | 604/96 |
| 5,236,424 | 8/1993 | Imran | 604/280 |
| 5,255,690 | 10/1993 | Keith et al. | 128/772 |
| 5,267,982 | 12/1993 | Sylvanowicz | 604/281 |
| 5,281,203 | 1/1994 | Reesemann | 604/164 |
| 5,297,346 | 3/1994 | Weiner | 33/512 |
| 5,330,466 | 7/1994 | Imran | 606/13 |
| 5,333,609 | 8/1994 | Bedingham et al. | 128/632 |
| 5,334,148 | 8/1994 | Martin | 604/194 X |
| 5,338,300 | 8/1994 | Cox | 606/194 X |
| 5,358,493 | 10/1994 | Schweich, Jr. et al. | 604/264 |
| 5,368,564 | 11/1994 | Savage | 604/95 |
| 5,383,923 | 1/1995 | Webster, Jr. | 607/125 |
| 5,385,562 | 1/1995 | Adams et al. | 604/280 |
| 5,399,164 | 3/1995 | Snoke et al. | 604/95 |
| 5,403,274 | 4/1995 | Cannon | 604/9 |
| 5,425,711 | 6/1995 | Ressemann et al. | 604/96 |
| 5,466,222 | 11/1995 | Reeseman et al. | 604/96 |
| 5,477,856 | 12/1995 | Lundquist | 128/642 |
| 5,545,136 | 8/1996 | Berger | 604/96 |
| 5,549,553 | 8/1996 | Ressemann et al. | 604/96 |
| 5,549,554 | 8/1996 | Miraki | 604/101 |
| 5,643,296 | 7/1997 | Hundertmark et al. | 604/22 X |
| 5,643,297 | 7/1997 | Nordgren et al. | 604/22 X |
| 5,645,533 | 7/1997 | Blaeser et al. | 604/164 |
| 5,667,488 | 9/1997 | Lundquist et al. | 604/22 |

FOREIGN PATENT DOCUMENTS 0 277 366 A1   8/1988   European Pat. Off. .
WO 96/23542   8/1996   WIPO .

*Primary Examiner*—Wynn Wood Coggins
*Assistant Examiner*—Cris L. Rodriguez
*Attorney, Agent, or Firm*—Crompton, Seager & Tufte, LLC.

[57] ABSTRACT

Catheter management system including a housing having a proximal end, a distal end and a chamber extending therethrough. A side port extends from the housing. A proximal fitting couples to the side port. A distal fitting is provided for coupling the chamber in fluid communication with a guide catheter. A releasable seal is positioned within the distal fitting for sealing about a device passing therethrough. A catheter storage mechanism is located at the housing proximal end in communication with the chamber.

28 Claims, 4 Drawing Sheets

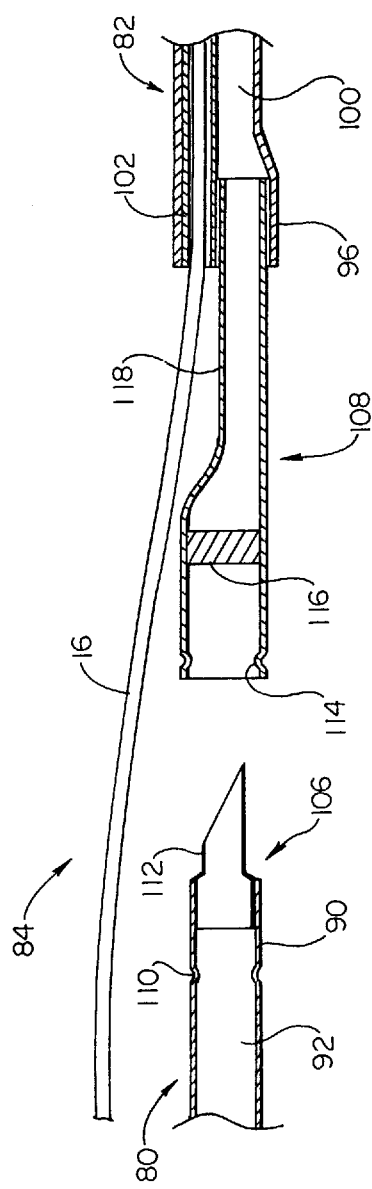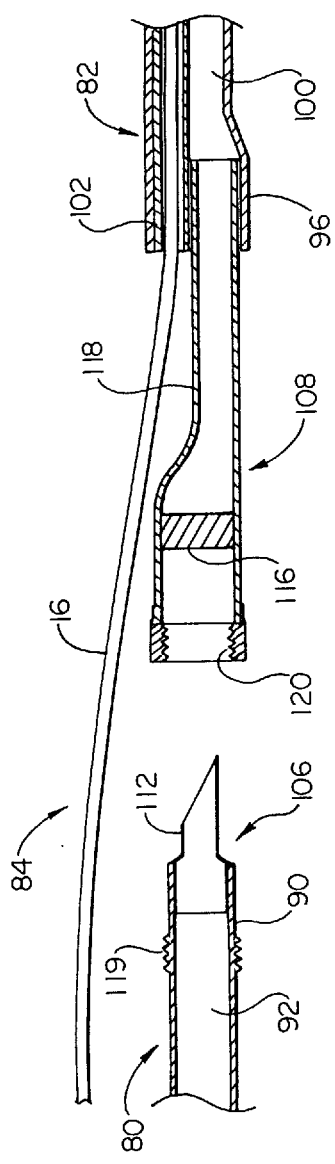

CATHETER MANAGEMENT SYSTEM

FIELD OF THE INVENTION

The present invention generally relates to ancillary devices for use with catheters. More particularly, the present invention relates to a catheter management system for use with intravascular catheters having a removable distal portion to facilitate catheter management and exchange procedures.

BACKGROUND OF THE INVENTION

Intravascular diseases are commonly treated by relatively non-invasive techniques, such as percutaneous transluminal coronary angioplasty (PTCA). PTCA is well known in the art and typically involves the use of a guide catheter, a guide wire and a balloon catheter, possibly in combination with other intravascular devices. A typical balloon catheter has an elongate shaft with a balloon attached proximate its distal end, and an inflation manifold attached proximate the proximal end. In use, the balloon catheter is advanced through a lumen in the guide catheter over the guide wire such that the balloon is positioned adjacent a restriction in a diseased vessel. The balloon is then inflated and the restriction in the vessel is opened.

One type of balloon catheter design is an over-the-wire type balloon catheter. An over-the-wire catheter typically includes a lumen extending therethrough adapted to receive a guide wire. Once a guide wire has been placed within a patient's vascular system, the over-the-wire type balloon catheter may be back-loaded onto the guide wire and advanced, tracking the guide wire, along the tortuous passages of a patient's vascular system until the balloon located at the distal end of the over-the-wire catheter is positioned across the stenosis.

The over-the-wire type intravascular catheter can be exchanged for a second balloon catheter without removing the guide wire. This allows an exchange of catheters without having to repeat the difficult and time consuming task of positioning the guide wire across a stenosis. In order to maintain the position of the guide wire within the patient's vascular system, a physician must hold onto a proximal end portion of the guide wire during the exchange procedure. To facilitate such an exchange procedure, a guide wire having a sufficiently long length (e.g., 300 cm) or a guide wire extension must be used such that the entire balloon catheter can be completely withdrawn over the guide wire, while maintaining position of the guide wire. The main disadvantage of this method is the length of the guide wire extending outside of the patient's body must be longer than the length of the balloon catheter being exchanged.

A variation of the over-the-wire balloon catheter which does not require such a long guide wire to facilitate the exchange of a first catheter with a second catheter is a balloon catheter having a single operator exchange type construction. A single operator exchange balloon catheter has at least one lumen extending over substantially the entire length of the catheter and a second shorter guide wire lumen. The second shorter guide wire lumen typically begins at a location close to a distal portion of the catheter, usually proximal of the balloon, and extends distally through the balloon and out an opening at the distal end of the balloon. With a single operator exchange type catheter, in order to maintain the position of the guide wire, it is only necessary that the length of the guide wire extending from the patient's body be longer than the length of the second guide wire lumen to facilitate an exchange procedure.

With the above described over-the-wire and single operator exchange type balloon catheters, a physician must still be able to handle the length of the balloon catheter removed from the patient's vascular system during exchange of a first catheter with a second catheter. A typical balloon catheter often exceeds 110 cm in length. It is often cumbersome for a physician and an attending assistant to maintain control of the length of the balloon catheter in exchanging a first balloon catheter for a second balloon catheter while holding the guide wire to maintain position of the guide wire across the stenosis.

Further, a PTCA procedure may be performed in either (or both) a proximal or distal portion of each of the coronary arteries, each requiring a different sized balloon catheter. There are anatomical differences between patients which may require a different shaped or different sized intravascular device for treatment.

To meet the above cited needs, balloon catheters are manufactured in various sizes and shapes as a total unit which is used once and discarded. However, often only a portion of each device is of different size or shape. For example, only the distal portion of a balloon catheter varies in shape and size depending on the given anatomical geometry to be navigated and the location of the stenosis receiving treatment, while the proximal portion of the balloon catheter is of the same size and is almost always a straight tubular member.

Accordingly, it is desirable to have a single operator exchange type balloon catheter which allows the use of a relatively short length of guide wire extending outside of the patient's body during a catheter procedure. It is desirable to have a catheter assembly which facilitates balloon catheter exchanges, wherein a distal portion of the balloon catheter may be changed to a different size as necessitated by the catheter procedure for use with a standard balloon catheter proximal portion. Further, it would be desirable to have a catheter management system which maintains organized control of the standardized proximal portion of the balloon catheter during exchange of an interchangeable distal portion in a balloon catheter exchange procedure.

SUMMARY OF THE INVENTION

The present invention is directed to a method and apparatus for performing a balloon angioplasty procedure, and for exchanging intravascular devices during the procedure. The present invention includes a catheter management system which may be used to facilitate exchange of a balloon catheter having an interchangeable distal portion, while maintaining the position of a guide wire in a patient's vascular system.

In one embodiment, the present invention includes a catheter management system. The catheter management system includes a housing having a proximal end, a distal end, and a chamber extending between the proximal end and the distal end. A side port extends from the housing, with a proximal fitting coupled to the side port. A distal fitting is provided for coupling the chamber in fluid communication with the guide catheter. A releasable seal is positioned within the distal fitting for sealing about a device passing therethrough. A catheter storage mechanism is located at the housing proximate and in communication with the chamber.

The catheter management system may further comprise a catheter assembly disposed within the chamber. The catheter assembly may include a proximal portion and a distal portion, wherein the distal portion is releasably coupled to the proximal portion. The catheter management system may further comprise a coupling mechanism for releasably coupling the proximal portion to the distal portion.

In one embodiment, the coupling mechanism is a notched coupling mechanism. It is recognized that other coupling mechanisms may be used, such as a threaded coupling mechanism.

The catheter management system may further include a luer mechanism extending through the housing in fluid communication with the balloon catheter proximal portion. The luer mechanism is rotatably connected to the balloon catheter proximal portion.

In one embodiment, the catheter assembly is a balloon catheter assembly. It is also recognized that the catheter assembly may be another type assembly such as a therapeutic, atherectomy, diagnostic, or ultrasonic catheter assembly.

The catheter storage system may include a take-up reel. The take-up reel includes a rotatable drum for storing the balloon catheter proximal portion wrapped about the drum.

BRIEF DESCRIPTION OF THE DRAWINGS

FIG. 3 is a partial longitudinal sectional view of one embodiment of the changeable distal portion coupling member of the catheter system in accordance with the present invention;

FIG. 4 is a partial longitudinal sectional view of another embodiment of the changeable distal portion coupling member of the catheter system in accordance with the present invention;

DETAILED DESCRIPTION OF THE PREFERRED EMBODIMENTS

The presently preferred embodiments and methodology described herein are applicable to coronary angioplasty procedures, and are specifically described in the context of dilatation balloon and guide catheters. It should be understood, however, that the embodiments and methodology of the present invention may be adapted for use with other types of intravascular therapeutic devices, such as atherectomy, diagnostic, and ultrasonic catheters.

Figure 1:
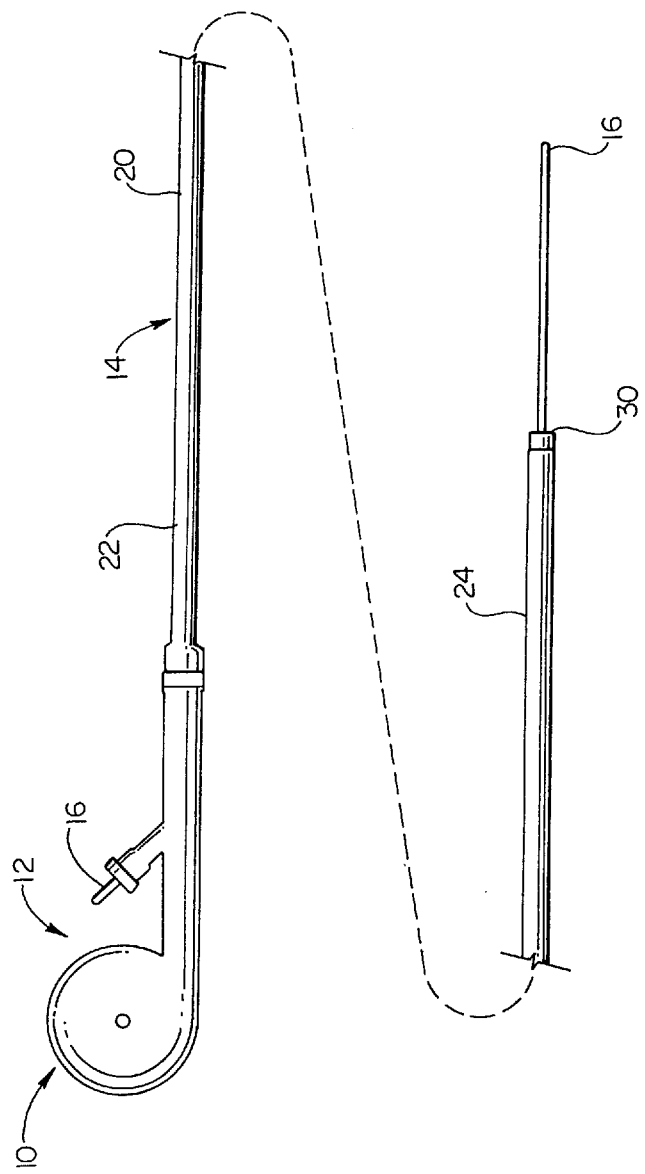
FIG. 1 is a side elevational view of one embodiment of a catheter system having a catheter management system in accordance with the present invention.

Referring to FIG. 1, a catheter assembly in accordance with the present invention is shown generally at 10. The catheter assembly 10 generally includes a catheter management system 12 coupled to a sheath or guide catheter 14. Extending through the catheter assembly 10 is a guide wire 16. Carried by the guide wire 16 is dilatation balloon catheter assembly 18 (shown in FIG. 2). The catheter assembly 10 includes a single operator exchange type catheter system having a catheter management system 12 for maintenance of a proximal portion of the dilatation balloon catheter 18 during exchange of a distal portion of the dilatation balloon catheter 18.

Guide catheter 14 includes a shaft 20 having a proximal end 22 and a distal end 24. A shaft lumen 26 (shown in FIG. 2) extends longitudinally through the shaft 20 from the proximal end 22 to the distal end 24. Operably connected to the proximal end 22 is catheter management system 12, which is in fluid communication with lumen 26 for connection to ancillary devices (not shown) for controlling the passage of such devices therethrough, and management of the dilatation balloon catheter 18 during an exchange procedure. Located at the distal end 24 of the shaft 20 is a soft tip 30. Soft tip 30 provides for atraumatic engagement of the ostium of the coronary artery receiving treatment.

In one embodiment, the guide catheter shaft 20 may be formed from an extrusion process, which may include a single or multi-layered design (not shown). In one preferred embodiment, the shaft 20 is formed from a multi-layered construction, which includes a first inner layer for decreasing the coefficient of friction within lumen 26 for passing a treatment device therethrough, and a second outer layer for stable positioning of the guide catheter shaft 20 and providing backout support during other treatment procedures. The first inner layer may be formed of polytetrafluoroethylene and may further include a hydrophilic coating, and the outer layer may be formed of polyethylene, polyurethane, polyether block amide, nylon or a blend of these. Shaft 20 may further include a third intermediate layer positioned between the first inner layer and the second outer layer formed of a braided construction for providing kink-resistance and torque control to the guide catheter 14.

Figure 2:
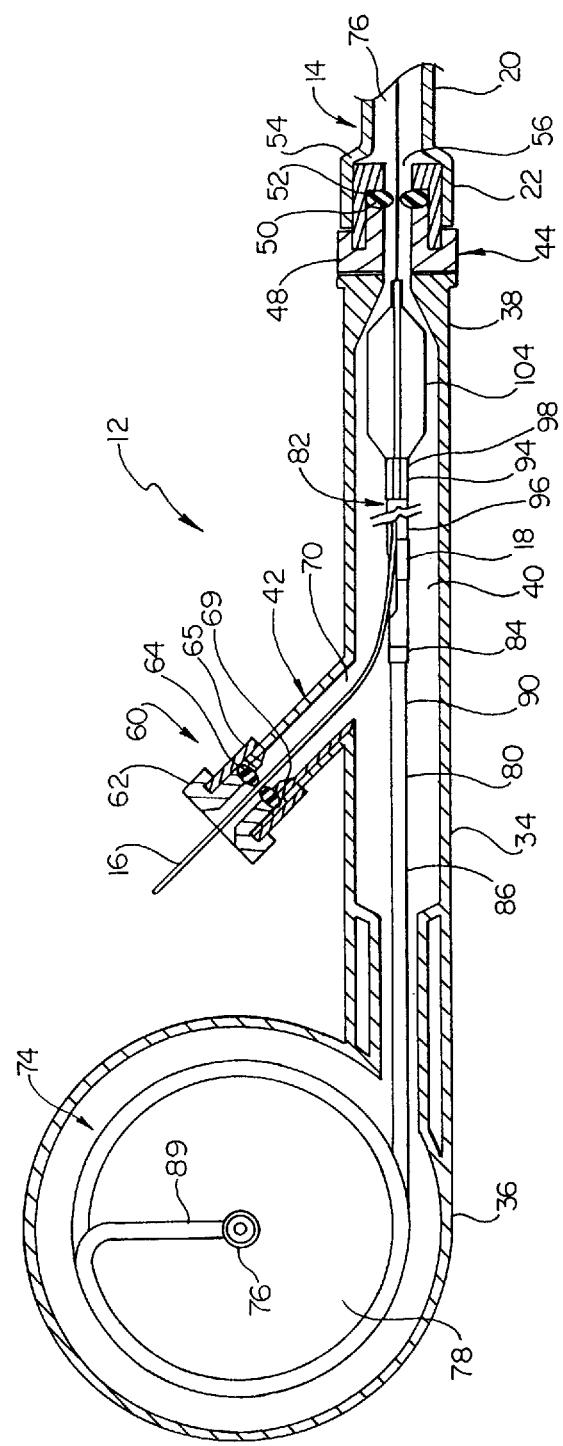
FIG. 2 is an enlarged longitudinal cross-sectional view of the proximal portion of the catheter management system shown in FIG. 1, having a dilatation balloon assembly with a changeable distal portion disposed therein.

Referring to FIG. 2, a longitudinal cross-section of the catheter management system 12 coupled to guide catheter 14 is shown. In a first embodiment, the catheter management system 12 generally includes a housing 34 having a proximal end 36 and a distal end 38. Extending through the housing 34 between the proximal end 36 and the distal end 38 is an exchange chamber 40. A side port 42 extends from catheter management system housing 34.

The catheter management system 12 is coupled to the guide catheter proximal end 22 using distal fitting 44. In one preferred embodiment, the fitting 44 is a Touey Borst fitting. The Touey Borst fitting generally includes a tightening mechanism 48, a seal 50, and a cylindrical member 52. The cylindrical member 52 further includes an inwardly extending flange 54. Fitting 44 is rotatably coupled to the housing distal end 38. The guide catheter proximal end 22 may be coupled to the cylindrical member 52.

Seal 50 is formed of a relatively soft durometer polymer such as polyurethane, and is secured to cylindrical member 52. In operation, tightening mechanism 48 may be rotated to move the tightening mechanism 48 into the cylindrical member 52, pressing seal 50 against radially inward extending flange 54. As seal 50 is pressed against the radially inward extending flange 54, seal 50 seals the longitudinally extending opening 56, and further locks or seals about any treatment devices passing therethrough (such as the guide wire 16 shown). Upon rotating the tightening mechanism 48 in an opposite direction, the seal 50 may be released.

Side port 42 extends from the catheter management system housing 34. Side port 42 is in fluid communication with the housing exchange chamber 40, and provides access to the exchange chamber 40 and shaft lumen 26 by ancillary treatment devices. Coupled to the end of side port 42 is proximal fitting 60, which can be similar in operation to fitting 44. In one preferred embodiment, the fitting 60 is a Touey Borst fitting. The proximal fitting 60 generally includes a tightening mechanism 62, a seal 64, and a cylindrical member 66 having an inwardly extending flange 68. Tightening mechanism 62 is rotatably coupled to cylindrical member 66, such as by threaded connection. Seal 64 is secured to the cylindrical member 66. Further, the cylindrical member 66 is securely attached to the side port 42.

In operation, as tightening mechanism 62 is rotated about a central longitudinal axis, the tightening mechanism 62 is fastened towards cylindrical member 66 pressing seal 64 against the radially inward extending flange 68. As seal 64 is pressed against the radially inward extending flange 68, the seal 64 seals off the side port 42 from lumen 70 and tightens/locks about any devices passing therethrough, such as the guide wire 16 shown. By rotating tightening mechanism 62 in an opposite direction, the seal 64 is released.

Located within the housing 34 at the proximal end 36 is take-up reel mechanism 74. Coupled to take-up reel mechanism 74 and extending through housing 34 is luer fitting 76. Luer fitting 76 couples to ancillary inflation devices (not shown) and is rotatably coupled to the take-up reel mechanism 74. In operation, take-up reel mechanism 74 includes a drum 78 which may be rotated by manual or electrical methods. A catheter shaft may be coupled to luer fitting 76. By rotating the take-up reel mechanism drum 78 in a first direction, the catheter shaft is wound about the drum 78 for storage. By rotating drum 78 in a second opposite direction, the catheter shaft may be unwound from drum 78 and extend distally from the assembly.

Dilatation balloon catheter assembly 18 is shown disposed within housing 34. Dilatation balloon catheter assembly 18 includes a standardized proximal portion 80 and a changeable distal portion 82. The proximal portion 80 is removably coupled to the distal portion 82 at coupling mechanism 84. Coupling mechanism 84 is described in further detail infra with respect to FIGS. 3 and 4. Although a dilatation balloon catheter assembly is shown disposed within housing 34, it is recognized that other assemblies or therapeutic devices may be disposed within housing 34, such as intravascular therapeutic devices, atherectomy, diagnostic, therapeutic or ultrasonic catheter assemblies.

Proximal portion 80 generally includes a shaft 86 having a proximal end 88 and a distal end 90 having an inflation lumen 92 (shown in FIG. 3) extending therethrough. Proximal end 88 is coupled to luer fitting 76 and distal end 90 is coupled to coupling mechanism 84. In one embodiment, the shaft 86 may be constructed of a super elastic alloy such as Nitinol or the shaft may be formed of a multi-layered coil covered by a polymer sheath, and is capable of being wound about the take-up reel mechanism drum 78.

Distal portion 82 generally includes a shaft 94 having a proximal end 96 and a distal end 98. Extending through shaft 94 is an inflation lumen 100 and a guide wire lumen 102 (shown in FIG. 3). Operably coupled to the shaft distal end 98 is balloon 104 which is in fluid communication with inflation lumen 100. Guide wire lumen 102 extends from a location proximal of balloon 104 through or adjacent balloon 104 through the balloon distal end. Distal portion 82 may be similar to the distal portion of single operator exchange balloon catheters as known in the art, such as two coaxial polymer tubes or a dual lumen extension.

Guide wire 16 may pass through side port 42, through the distal portion guide wire lumen 102 and extend longitudinally through the guide catheter shaft lumen 26.

Referring to FIG. 3, one embodiment of a coupling mechanism 84 is shown. Coupling mechanism 84 allows proximal portion 80 to be releasably coupled to distal portion 82. Coupling mechanism 84 further provides a fluid-tight connection between the proximal portion inflation lumen 92 and the distal portion inflation lumen 100.

Coupling mechanism 84 generally includes first coupling mechanism 106 and second coupling mechanism 108. First coupling mechanism 106 is secured to the proximal portion distal end 90. Second coupling mechanism 108 is a generally tubular member which is secured to the distal portion proximal end 96. The first coupling mechanism 106 is insertable within the second coupling mechanism 108, and further includes a locking notch 110 and a piercing member 112. Second coupling mechanism 108 further includes a locking barb or dimple 114 and a seal 116. Second coupling mechanism 108 further includes a reduced diameter portion 118 for allowing guide wire 16 to enter the distal portion guide wire lumen 102.

In operation, the first coupling mechanism 106 is inserted within the second coupling mechanism 108. As first coupling mechanism 106 enters second coupling mechanism 108, piercing member 112 pierces the seal 116, allowing fluid communication between the proximal portion inflation lumen 92 and the distal portion inflation lumen 100. The first coupling mechanism 106 is further inserted within second coupling mechanism 108 "snap locking" or "twist locking" the locking barb or dimples 114 within locking notch 110, securely coupling the first coupling mechanism 106 to the second coupling mechanism 108. In one embodiment, locking notch 110 includes a fail safe locking channel to accomplish this purpose. Proximal portion 80 is now releasably locked to distal portion 82. To unlock the proximal portion 80 from the distal portion 82, the first coupling mechanism 106 and second coupling mechanism 108 may be "snap locked" or "twist locked" in an opposite direction, releasing the coupling between the first coupling mechanism 106 and the second coupling mechanism 108.

Referring to FIG. 4, it is recognized that alternative coupling mechanisms may be used for releasably coupling the proximal portion 80 to the distal portion 82. In the embodiments shown, coupling mechanism 84 includes threaded member 119 and rotatable threaded member 120. By rotatably coupling first coupling mechanism 106 to second coupling mechanism 108, threaded member 119 and threaded member 120 provide a fluid tight connection between first coupling mechanism 106 and second coupling mechanism 108. To release first coupling mechanism 106 from second coupling mechanism 108, rotatable threaded member 120 is simply rotated in an opposite direction.

Figure 5:
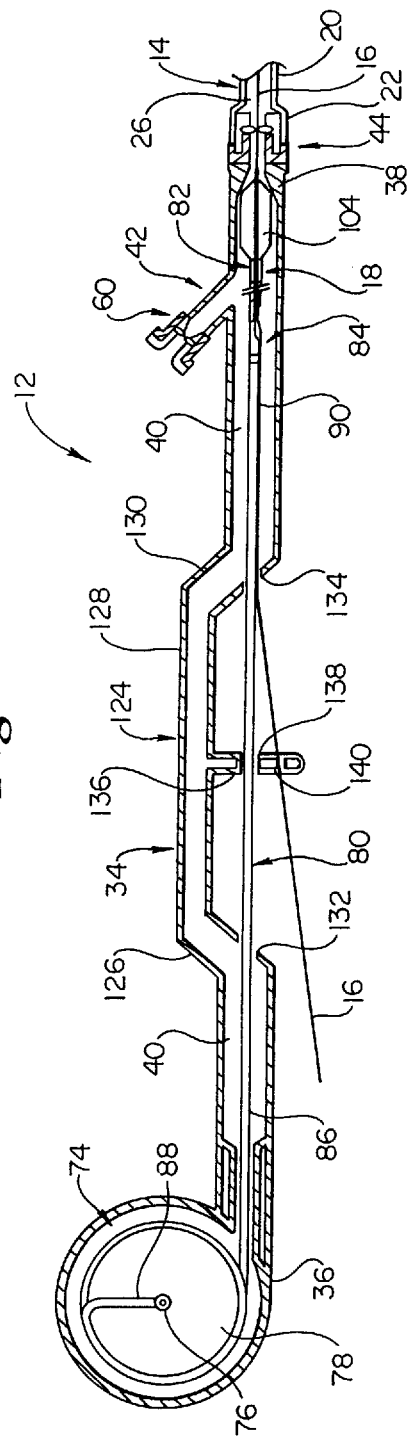
FIG. 5 is a longitudinal cross-sectional view of the proximal portion of another embodiment of the catheter management system in accordance with the present invention, having a dilatation balloon assembly with a changeable distal portion disposed therein.

FIG. 5 illustrates an alternative embodiment of the catheter assembly 10 including the catheter management system 12 shown in FIGS. 1 and 2. Since this embodiment can be similar to the previously described embodiment, similar parts appearing in FIG. 5 are represented by the same, corresponding reference numeral.

Referring to FIG. 5, another embodiment of the catheter management system 12 is generally shown in longitudinal cross-sectional view, having dilatation balloon catheter assembly 18 with a standardized proximal portion 80 and changeable distal portion 82 disposed therein. In this embodiment, housing 34 includes a cartridge handle 124 located intermediate the housing proximal end 36 and housing distal end 38. The cartridge handle 124 generally includes a proximal leg 126, an intermediate member 128, and a distal leg 130. Proximal leg 126 includes proximal leg opening 132, and distal leg 130 includes distal leg opening 134.

Extending downward from the intermediate member 128 is extension guide 136. Extension guide 136 includes a proximal portion opening 138 and a guide wire locking mechanism 140. In operation, the proximal portion shaft 86 exits chamber 40 through proximal leg opening 132, through proximal portion 138, and re-enters chamber 40 through distal leg opening 134. Guide wire 16 is releasably lockable within guide wire locking mechanism 140, and may pass through guide wire locking mechanism 140 into chamber 40 through distal leg opening 134 adjacent the shaft 86. Guide wire locking mechanism 140 operates similar to fitting 60 (previously described herein) for maintaining guide wire 16 stationary relative to guide catheter 14 during advancement or exchange of the distal portion 82 of dilatation balloon catheter assembly 18.

Figure 6:
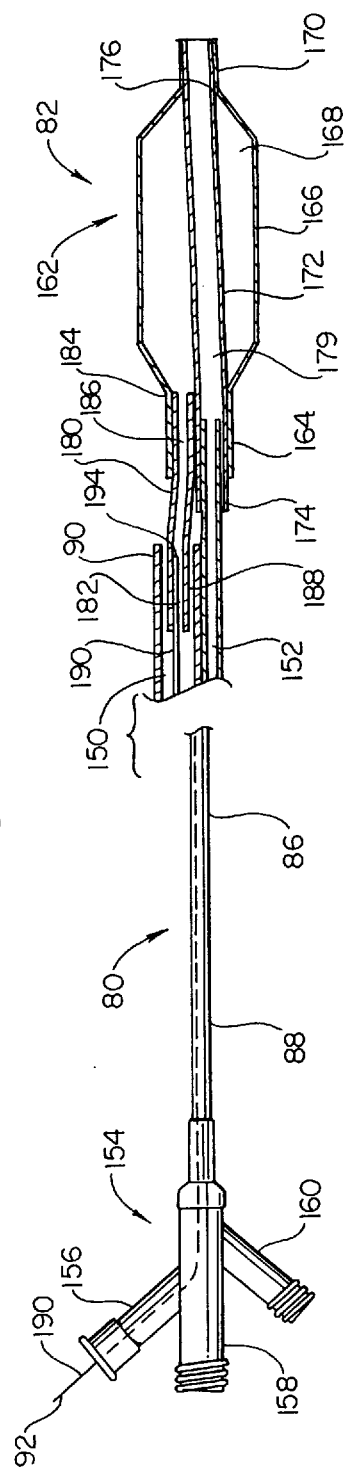
FIG. 6 is a side longitudinal sectional view of another embodiment of a dual lumen catheter system having a changeable distal portion in accordance with the present invention.

Referring to FIG. 6, another embodiment of the dilatation balloon catheter assembly 18 having distal portion 82 which may be releasably sealed to proximal portion 80, in accordance with the present invention is shown. The dilatation balloon catheter assembly 18 is a dual lumen catheter, including an inflation lumen isolated from a separate guide wire lumen. The distal catheter portion 82 is releasably connected to the proximal catheter portion 80, allowing for balloon inflation/deflation and easy exchange of the distal catheter portion 82. The proximal catheter portion 80 may be resterilized and reused, with other distal catheter portions 82.

The proximal portion shaft 80 includes an inflation lumen 150 and a guide wire lumen 152 extending between the proximal end 88 and the distal end 90. Coupled to the proximal end 88 is a Y-adapter manifold assembly 154. Y-adaptor assembly 154 includes a first side port 156, central port 158 and second side port 160 for connection to ancillary devices.

The distal portion 82 generally includes a balloon system 162 having a proximal neck portion 164, balloon 166 with an interior chamber 168 and a distal neck portion 170. Proximal neck portion 164 is generally tubular shaped and extends proximal from balloon 166. Distal neck portion 170 is generally tubular shaped and extends distally from balloon 166.

The distal portion 82 further includes a support member 172. In the embodiment shown in FIG. 6, the support member 172 is a generally tubular member including a proximal end 174, a distal end 176 and a lumen 178 extending therethrough. The support member 172 extends through the balloon interior chamber 168, and is secured to the proximal neck portion 164 proximate its proximal end 174 and is secured to the distal neck portion 170 proximate the distal end 176. The outside diameter of support member 172 is less than the inside diameter of proximal neck portion 164, and proximate the inside diameter of distal neck portion 170. At distal neck portion 170, the support member 172 is sealed about the interior periphery of the distal neck portion 170.

An inflation extension shaft 180 extends proximally from proximal neck portion 164. The inflation extension shaft includes a proximal end 182, a distal end 184 and has a lumen 186 extending therethrough. The inflation extension shaft lumen 186 is in fluid communication with balloon interior chamber 168.

The inflation extension shaft distal end 184 is sealed to an interior wall of the balloon system proximal neck portion 164 and located adjacent support member 172.

Located proximal to the inflation extension shaft proximal end 182 is seal member 188. The seal member 188 is located about the exterior periphery of inflation extension shaft 180. The seal member 188 releasably seals the inflation extension shaft 180 within inflation lumen 150, allowing movement of the distal portion 82 relative to the proximal portion 80 while inhibiting inflation fluid from exiting the proximal portion of shaft 86.

In a first embodiment, the seal member 188 may be an interference type seal, such as an O-ring seal, and formed of a relatively soft durometer polymeric material, such as polyurethane. The seal member 188 outer diameter is closely sized to fit the inner diameter of shaft 86 inflation lumen 150 to create an interference fit which allows slidable movement of the inflation extension shaft 180 relative to the proximal portion shaft 86. When balloon 166 is inflated with fluid, the seal member 188 between the inflation extension shaft 180 and inflation lumen 150 inhibits inflation fluid from exiting the inflation lumen 150 through distal end 90. In another embodiment, it is recognized that seal member 188 may be an alternative type seal, such as a tolerance fit, collar, bladder, or valve type sealing member such as those disclosed in U.S. Pat. No. 5,490,837 to Blaeser et al. which is herein incorporated by reference.

Operably coupled to distal portion 82 is push member 190. Push member 190 includes a push member proximal end 192 and a push member distal end 194. The push member distal end 194 is coupled to the interior wall of inflation extension shaft 180. In one embodiment, the push member distal end 194 is bonded to the inflation extension shaft 180 interior wall using an adhesive. The push member 190 extends longitudinally proximal of the inflation shaft 180 through the proximal portion of shaft inflation lumen 150 with the push member proximal end 192 extending proximally from the proximal end 88 and exiting the catheter assembly 18 through first side port 156. The push member 190 provides movement and control of the distal portion 82 relative to the proximal portion 80 from a location proximal of the Y-adaptor manifold assembly 154.

In assembly of guide catheter assembly 18, the push member proximal end 192 is inserted within inflation lumen 150 at the shaft distal end 90. Push member 190 is passed through the inflation lumen 150 until the push member proximal end 192 exits the Y-adaptor manifold assembly side port 156.

As push member 190 is further pulled proximally of Y-adaptor manifold assembly 104, the inflation extension shaft proximal end 182 is positioned within inflation lumen 150 and the guide wire lumen 152 is inserted within the support member proximal end 174. As inflation extension shaft 180 is pulled into inflation lumen 150, seal member 188 operates to provide a fluid-tight seal between the inflation extension shaft 180 and inflation lumen 150. Catheter assembly 18 may now be loaded onto a previously placed guide wire within a patient's vascular system for treatment of a diseased vessel.

If it is desirable to exchange the distal portion 82 for a second distal portion, the catheter assembly 18 is withdrawn from the patient's vascular system. Push member 190 may be operated to release the seal between seal member 188 and inflation lumen 150. Distal portion 82 is withdrawn from the shaft distal end 90. A second distal portion may now be backloaded and releasably sealed to the proximal portion 80 through the shaft distal end 90 as previously described herein. The distal catheter portion 82 may be releasably connected to the proximal catheter portion 80, allowing for balloon inflation/deflation and easy exchange of the distal catheter portion 82. The proximal catheter portion 80 may be resterilized and reused with other distal catheter portions 82.

Referring to FIG. 1, in operation of the catheter assembly 10, intravascular access is initially made in a conventional manner. For use in an angioplasty procedure, the patient's femoral artery is entered percutaneously, and a sheath is inserted for access to the vascular system. Although the angioplasty procedure described herein utilizing the femoral artery to access the patient's vascular system is the most common method, it is also recognized that the present invention may be used for brachial and radial artery access using similar procedures. It is also recognized that the present invention may be used in non-coronary procedures, such as PTA, cerebral or other non-vascular procedures.

A guide catheter placement guide wire is preferably inserted into the guide catheter lumen 26 while the entire guide catheter 14 is outside the body, such that the distal tip of the guide wire extends beyond the guide catheter 14. The combination of the guide catheter 14 and the guide wire is then advance to the desired location in the vascular system, in particular, it is advanced through the femoral artery and up over the aortic arch. The guide wire may be inserted into the vessel prior to advancement of the guide catheter 14 over the guide wire, or the guide catheter 14 can be inserted into the vessel prior to advancement of the guide wire through lumen 26. The guide catheter placement guide wire is removed and guide wire 16 is inserted into the guide catheter 14 and advanced until the distal end of guide wire 16 is located proximate the guide catheter distal end 24.

The guide catheter 14 may be advanced to deepseat the guide catheter soft tip 30 in the ostium of the coronary to receive treatment. The guide wire 16 may further be advanced beyond the guide catheter distal end 24 and positioned across the stenosis receiving treatment.

Referring also to FIG. 2 or FIG. 5, the catheter management system 12 is coupled to the guide catheter proximal end 22 at distal fitting 44 with guide wire 16 inserted through the housing exchange chamber 40 exiting side port 42. It is recognized that the catheter management system 12 may be coupled to the guide catheter 14 before insertion and positioning of the guide catheter 14 and guide wire 16 within the patient's vascular system. Further, it is recognized that the dilatation balloon catheter 18 standardized proximal portion 80 may be coupled to the changeable distal portion 82 before the catheter management system 12 is coupled to the guide catheter proximal end 22.

Once a path across the stenosis has been established, the distal fitting 44 is operated to tighten/lock seal 50 about the guide wire 16. The dilatation balloon catheter assembly distal portion 82 is loaded onto the proximal end of guide wire 16 and passed through side port 42 and exchange chamber 40 until the balloon 104 is positioned proximal of distal fitting seal 50.

The dilatation balloon catheter assembly proximal portion 80 may now be coupled to the distal portion 82. The take-up reel mechanism 74 is operated to extend the proximal portion shaft distal end 90 to meet the distal portion proximal end 96. Coupling mechanism 84 is now operated, such as by methods previously described herein, to couple the proximal portion 80 to the distal portion 82, wherein the proximal portion inflation lumen 92 is in fluid communication with the distal portion inflation lumen 100.

The fitting 44 tightening mechanism 48 is operated to release seal 50 about guide wire 16. The fitting 60 tightening mechanism 62 (located at side port 42) is operated to seal the seal 64 about guide wire 16 at side portion 42. (Similarly, in reference to FIG. 5, guide wire locking mechanism 140 is operated to lock guide wire 16.) The catheter management system 12 may now be operated to position the dilatation balloon catheter assembly 18 within the patient's vascular system. Take-up reel mechanism 74 is now operated to extend the distal portion of shaft 86 distally for placement of the balloon 104 across the stenosis region.

Lure fitting 76 is coupled to an inflation source. Balloon 104 may now be inflated and deflated as necessary for treatment of the stenosed region. Upon completion of treatment using balloon 104, inflation fluid is removed through lure fitting 76 to deflate the balloon 104. Take-up reel mechanism 74 may be operated to pull the dilatation balloon catheter assembly 18 back through the guide catheter lumen 26 until the balloon 104 is positioned proximal of fitting 44. As the dilatation balloon catheter assembly 18 is pulled back through guide catheter 14 by the catheter management system 12, the take-up reel mechanism 74 stores the proximal portion 86 about drum 78.

The tightening mechanism 48 of distal fitting 44 is now operated to lock the seal 50 about guide wire 16. The tightening mechanism 62 of proximal fitting 60 (or locking mechanism 140 of FIG. 5) is operated to release the locking seal of seal 64 about the guide wire 16 (at side port 42). Further, coupling mechanism 84 is operated to release the proximal portion 80 from the distal portion 82 by methods as previously described herein.

Distal portion 82 may now be removed from the guide wire 16 by tracking the guide wire 16 and exiting through side port 42. The position of guide wire 16 within the patient's vascular system is maintained, since the guide wire 16 is tightly locked and retained by distal fitting 44. If necessary for exchanging a first catheter for a second catheter, a second distal portion 82 may be back-loaded onto the guide wire 16 and coupled with the proximal portion 86 using the same method as previously described herein.

Although the present invention has been described with reference to preferred embodiments, those skilled in the art will recognize that changes may be made in form and detail without departing from the spirit and scope of the invention. As such, it is intended that the foregoing detailed description be regarded as illustrative, rather than limiting and that it is the following claims, including all equivalents thereof, which are intended to define the scope of the invention.

What is claimed is:

1. A catheter management system comprising:
    a housing having a proximal end, a distal end, and a chamber extending between the proximal end and the distal end;
    a distal fitting for coupling the chamber in fluid communication with a guide catheter;
    a catheter storage mechanism located within the housing proximal end in communication with the chamber; and
    a releasable seal positioned within the distal fitting for sealing about a device passing therethrough.

2. The catheter system of claim 1, wherein the catheter management system includes a take-up reel.

3. The catheter management system of claim 2, wherein the take-up reel includes a rotatable drum for storing the catheter proximal portion about the drum.

4. The catheter management system of claim 1, further comprising a side port extending from the housing.

5. The catheter management system of claim 1, further comprising a proximal fitting coupled to the side port.

6. The catheter management system of claim 5, wherein the proximal fitting is a Touhy-Borst fitting.

7. The catheter management system of claim 1, wherein the distal fitting is a Touhy-Borst fitting.

8. A catheter management system comprising:

a housing having a proximal end, a distal end, and a chamber extending between the proximal end and the distal end;

a distal fitting for coupling the chamber in fluid communication with a guide catheter;

a catheter storage mechanism located within the housing proximal end in communication with the chamber; and a catheter assembly disposed within the chamber including a proximal portion and a distal portion, wherein the distal portion is releasably coupled to the proximal portion.

9. The catheter management system of claim 8, further comprising a coupling mechanism for releasably coupling the proximal portion to the distal portion.

10. The catheter management system of claim 9, the coupling mechanism further comprising:

a first member extending distally from the proximal portion; and a second member extending proximally from the distal portion;

wherein the first member is insertable within the second member for releasably locking the first member within the second member.

11. The catheter management system of claim 9, wherein the coupling mechanism is a threaded coupling mechanism.

12. The catheter management system of claim 8, wherein the distal portion is a single operator exchange design.

13. The catheter management system of claim 8, further comprising a luer mechanism extending through the housing in fluid communication with the proximal portion.

14. The catheter management system of claim 13, wherein the luer mechanism is rotatably connected to the proximal portion.

15. The catheter management system of claim 8, wherein the catheter assembly is a balloon catheter assembly.

16. A catheter assembly comprising:

a proximal catheter member having a proximal end, a distal end, and a lumen extending longitudinally therethrough:

a distal catheter member having a proximal end, a distal end, and a lumen extending longitudinally therethrough, wherein the distal catheter member is releasably coupled in fluid communication with the proximal catheter member; and a catheter management system coupled to the proximal catheter member.

17. The catheter assembly of claim 16, further comprising a coupling mechanism for releasably coupling the distal catheter member with the proximal catheter member.

18. The catheter assembly of claim 16, wherein the distal catheter member further comprises a distal balloon catheter assembly having a balloon coupled to the distal end of the distal catheter member, wherein the balloon is in fluid communication with the proximal catheter member.

19. A catheter assembly comprising:

a proximal catheter member having a proximal end, a distal end, and a lumen extending longitudinally therethrough;

a distal catheter member having a proximal end, a distal end, and a lumen extending longitudinally therethrough, wherein the distal catheter member is releasably coupled in fluid communication with the proximal catheter member;

a catheter management system coupled to the proximal catheter member; and a coupling mechanism for releasably coupling the distal catheter member with the proximal catheter member, wherein the coupling mechanism is a notched releasable locking mechanism.

20. A catheter assembly comprising:

a proximal catheter member having a proximal end, a distal end, and a lumen extending longitudinally therethrough:

a distal catheter member having a proximal end, a distal end, and a lumen extending longitudinally therethrough, wherein the distal catheter member is releasably coupled in fluid communication with the proximal catheter member;

a catheter management system coupled to the proximal catheter member; and a coupling mechanism for releasably coupling the distal catheter member with the proximal catheter member, wherein the coupling mechanism is a threaded releasable locking mechanism.

21. A catheter assembly comprising:

a proximal catheter member having a proximal end, a distal end, and a lumen extending longitudinally therethrough:

a distal catheter member having a proximal end, a distal end, and a lumen extending longitudinally therethrough, wherein the distal catheter member is releasably coupled in fluid communication with the proximal catheter member;

a catheter management system coupled to the proximal catheter member, and a take-up reel for storing the proximal catheter member.

22. A catheter assembly comprising:

a proximal catheter member having a proximal end, a distal end, and a lumen extending longitudinally therethrough:

a distal catheter member having a proximal end, a distal end, and a lumen extending longitudinally therethrough, wherein the distal catheter member is releasably coupled in fluid communication with the proximal catheter member;

a catheter management system coupled to the proximal catheter member, wherein the catheter management system includes a housing having a proximal end, a distal end, and an exchange chamber extending therethrough, and a take-up reel rotatably coupled within the proximal end of the housing.

23. The catheter assembly of claim 22, wherein the catheter management system further comprises an inflation luer extending through the housing rotatably coupled to the proximal end of the proximal catheter member.

24. The catheter assembly of claim 22, wherein the catheter management system further comprises a distal lockable fitting coupled to the distal end of the housing.

25. The catheter assembly of claim 24, wherein the distal lockable fitting releasably couples to a guide catheter.

26. The catheter assembly of claim 24, wherein the distal lockable fitting releasably couples to a device passing therethrough.

27. The catheter assembly of claim 22, wherein the catheter management system further comprises a side port extending from the housing in fluid communication with the exchange chamber.

28. The catheter assembly of claim 27, wherein the catheter management system further comprises a proximal lockable fitting coupled to the side port.

* * * * *